United States Patent [19]

McCourry et al.

[11] 4,178,947
[45] Dec. 18, 1979

[54] TENSIONING DEVICE FOR A DENTAL FLOSSING APPARATUS

[76] Inventors: Phyllis J. McCourry, 3306 McCourry St., Bakersfield, Calif. 93304; Victoria L. Fuhrman, 4506 Knoll Dr., Bakersfield, Calif. 93308

[21] Appl. No.: 874,261

[22] Filed: Feb. 1, 1978

[51] Int. Cl.² ............................................ A61C 15/00
[52] U.S. Cl. ................................................. 132/92 R
[58] Field of Search .................... 132/89, 91, 92 R; 32/40 R

[56] References Cited

U.S. PATENT DOCUMENTS

| | | | |
|---|---|---|---|
| 2,217,917 | 10/1940 | Munro | 132/92 R |
| 3,340,881 | 9/1967 | Cowan | 132/92 R |

*Primary Examiner*—Robert Peshock
*Attorney, Agent, or Firm*—W. Edward Johansen

[57] ABSTRACT

The present invention is an improved tensioning mechanism for use in a dental flossing apparatus. The dental flossing apparatus is used in conjunction with a dental floss container, which has an inner lip and which contains a spool of dental floss. The tensioning mechanism includes a first elongated member and a second elongated member, each of which has a first end and a second end and each of which has a raised tip-portion at its second end which has a hole disposed perpendicularly thereto and adapted to receive the dental floss therethrough. The second elongated member is formed so that it is pivotally coupled to the first elongated member in a scissor-like manner the raised tip-portions of the first and second elongated members will separate from each other when their first ends are brought together. The tensioning mechanism also includes a dispensing mechanism for controlling the dispensing of dental floss from the dental floss container. The dispensing mechanism includes a shaft, which is adapted to be forceably engaged into the dental floss spool, a disc, which is adapted to travel along the inner lip of the dental floss container and which is fixedly coupled to the shaft, and a spool, which is adapted to receive used dental floss and which is mechanically coupled to the shaft by means of a ratchet assembly, which permit rotation in only one direction.

2 Claims, 8 Drawing Figures

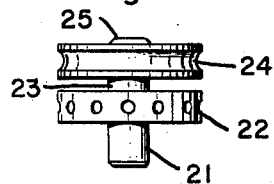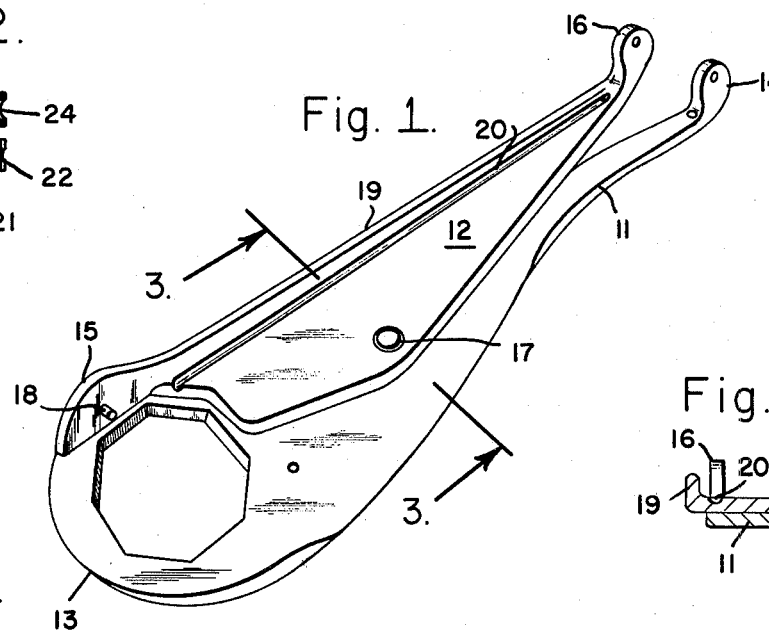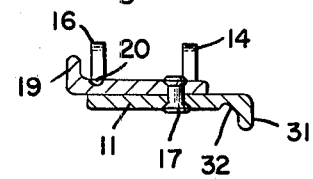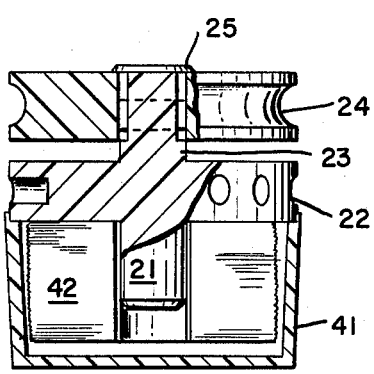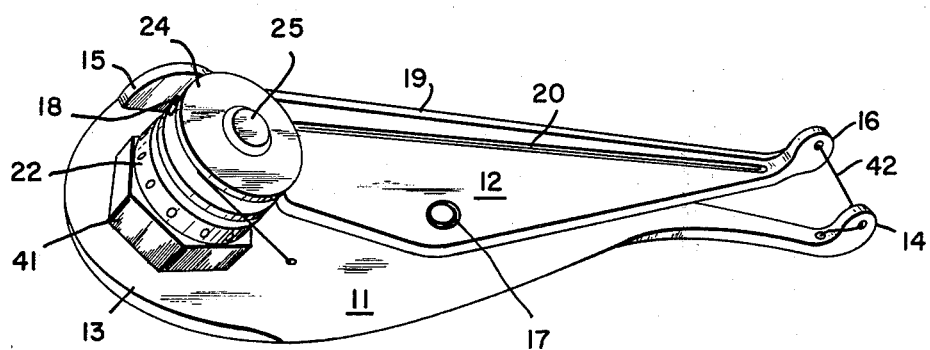

TENSIONING DEVICE FOR A DENTAL FLOSSING APPARATUS

BACKGROUND OF THE INVENTION

1. Field of the Invention

The present invention relates to a dental floss holding apparatus, and more particularly to an improved tensioning mechanism for use in the dental floss holding apparatus.

2. Description of the Prior Art

U.S. Pat. No. 2,187,442, entitled Dental Floss Holder, issued to John B. Beach on Jan. 16, 1940, teaches a dental floss holding apparatus that includes a first mechanical mechanism which maintains a length of dental floss in a tant condition and a second mechanical mechanism which feeds fresh dental floss to the first mechanical mechanism. This dental floss holding apparatus not only does not hold the dental floss tant enough, but it also is not a compact holding apparatus so that a user cannot use the apparatus with any dexterity.

U.S. Pat. No. 2,217,917, entitled Dental Floss Holder, issued to Harold W. Munro on Oct. 15, 1940, teaches a dental floss holder that is more compact than the dental floss holding apparatus described above, but it does not provide force to hold the dental floss tant enough. Another difficulty with dental floss holder is that if the length of dental floss which is cleaning is too long then its user tends to saw his gums.

U.S. Pat. No. 3,311,116, entitled Dental Floss Holder and Dispenser, issued to Talmadge E. Foster on Mar. 28, 1967, teaches a dental floss holder that has two handles which may be moved together to grippingly engage dental floss which extends through channels and slots and is disposed between the handles, which, when released, move apart by spring action to release the dental floss. This dental floss holder not only does not hold the dental floss tant enough, but it also leaves too long a length of dental floss exposed so that its user has a tendancy to (saw) use a sawing motion with the length of dental floss, rather than floss with it. The inventors point out that the tantness of the length of dental floss is only necessary to force it between the teeth and that this tantness should be reduced after the length of dental floss is between the teeth so that the length of dental floss may travel up and down each side of each tooth in and out of the (gums) gingival sulcus.

U.S. Pat. No. 2,837,098, entitled Dental Floss Holder and dispenser, issued to William M. Sorboro on June 3, 1958, teaches a dental floss holder which includes a ratchet-equipped head that has ratchet teeth which cooperate releaseably and retentively with a socket in the dental floss holder. The difficulty with this ratchet-equipped head is that it cannot apply enough tension to allow the user to force the dental floss between his teeth.

U.S. Pat. No. 3,993,085, entitled Dental Floss Applicator, issued to Edward T. Skinner on Nov. 23, 1976, teaches a dental floss applicator that includes a thumb wheel advancer for securing the end of the dental floss and a slidable tension bar for applying tension on the dental floss across a u-shaped collar. One of the difficulties with this dental floss applicator is that it uses too much dental floss. Another difficulty is that unused dental floss is exposed and may become unsanitary.

U.S. Pat. Nos. 4,006,750, 3,834,404, 4,002,183, and 4,041,962, all teach dental floss holders which are lightweight and compact, but none of these holders provide enough tantness in the dental floss and convenience for use in conjunction with a dental floss container.

U.S. Pat. No. 4,004,599, entitled Dental Floss Holder, issued Marvin L. Rosenfield on Jan. 25, 1977, teaches a dental floss holder that includes a tensioning mechanism. U.S. Pat. No. 2,544,276, entitled Dental Floss Holder, issued to Robert A. Ness on Mar. 6, 1951, teaches another dental floss holder that includes a tensioning mechanism. U.S. Pat. No. 4,051,857, entitled Dental Floss Holder, issued to James B. Zambito on Oct. 4, 1977, teaches an adjustable handle for a dental floss holder.

U.S. Pat. No. 3,858,595, entitled Holder for Using and Tensioning Dental Floss, issued to George Ensminger on Jan. 7, 1975, teaches a dental floss holder that a user maintains the floss span by finger pressure. U.S. Pat. No. 4,052,994, entitled Dental Floss Applicator, issued to Floyd A. Thun on Oct. 11, 1977, teaches a dental floss applicator that has a receptacle for receiving a spool of dental floss therein and rewind and tension means associated with the receptacle and receptacle closure top for maintaining the dental floss under a certain degree of tension. A projecting holder from the receptacle top has two spaced tines extending therefrom for stretching a piece of clean dental floss therebetween. The structure is so designed that additional tension may be applied to the stretched piece of dental floss by the user's index finger while holding the applicator in one hand in an easy and comfortable manner.

U.S. Pat. Nos. 4,031,908, 4,005,721, and 4,031,909, all teach dental floss holders which include containers incorporated therein.

A common problem with known dental floss holders and the like is that they fail to provide sufficient tension upon the dental floss being used therewith in order to properly clean a user's teeth and (gums) gingival sulcus. It is very desirable that an easy means for varying the amount of tension be provided in order to make it handy and convenient for the user of the device to vary same.

Another problem with known prior art devices is that they are inconvenient and awkward to use. Furthermore, many of these devices fail to provide rewind mechanism in order to take up excess slack if such should occur. With device not providing such a rewind structure, the excess dental floss must be cut off and is thus obviously wasted. This is both expensive, annoying, and inconvenient.

Another problem with known prior art devices is that they fail to permit use of the dental floss spool just as it comes from the manufacturer and is sold by the retail outlet.

SUMMARY OF THE INVENTION

In view of the factors and conditions characteristic of the prior0 art it is a primary object of the present invention to provide an improved tensioning mechanism for a dental flossing apparatus that cannot only hold a length of dental floss tant enough so that a user can force the length of dental floss between his teeth, but can also relax the tension in the length of the dental floss so that the user may floss his teeth without cutting into (his gums) the gingiva.

It is another object of the present invention to provide an improved tensioning mechanism for a dental flossing apparatus which first tightens the length of dental floss to a low level of tension and then allows the user to vary the tension in the length of dental floss.

It is still another object of the present invention to provide an improved tensioning mechanism for a dental flossing apparatus which not only keeps the unused dental floss from being exposed, but also reduces the amount of dental floss that is used in each flossing.

It is yet another object of the present invention to provide an improved tensioning mechanism for a dental flossing apparatus which incorporates not only the dental floss spool, but also the dental floss container, which becomes a part of the improved tensioning mechanism.

In accordance with a preferred embodiment of the present invention is an improved tensioning mechanism for use in a dental flossing apparatus. The dental flossing apparatus is used in conjunction with a dental floss container, which has an inner lip and which contains a spool of dental floss. The tensioning mechanism includes a first elongated member and a second elongated member, each of which has a first end and a second end and each of which has a raised tip-portion at its second end which has a hole disposed perpendicularly thereto and adapted to receive the dental floss therethrough. The second elongated member is formed so that it is pivotally coupled to the first elongated member in a scissor-like manner the raised tip-portions of the first and second elongated members will separate from each other when their first ends are brought together. The tensioning mechanism also includes a dispensing mechanism for controlling the dispensing of dental floss from the dental floss container. The dispensing mechanism includes a shaft, which is adapted to be forceably engaged into the dental floss spool, a disc, which is adapted to travel along the inner lip of the dental floss container and which is fixedly coupled to the shaft, and a spool, which is adapted to receive used dental floss and which is mechanically coupled to the shaft by means of a ratchet assembly, which permit rotation in only one direction.

The features of the present invention which are believed to be novel are set forth with particularity in the appended claims.

Other objects and many of the attendant advantages will be more readily appreciated as the same becomes better understood by reference to the following detailed description and considered in connection with the accompanying drawing in which like reference symbols designate like parts throughout the figures.

DESCRIPTION OF THE DRAWING

FIG. 1 is a perspective view of a dental flossing apparatus which incorporates an improved tensioning mechanism therein in accordance with the principles of the present invention after its ratchet mechanism has been removed.

FIG. 2 is an elevational view of the ratchet mechanism of the tensioning mechanism of FIG. 1.

FIG. 3 is a cross-sectional view of the dental flossing apparatus of FIG. 1 along the line 3—3.

FIG. 4 is a cross-sectional view of the ratchet mechanism of FIG. 2 along the line 4—4.

FIG. 5 is an enlarge, fragmentary cross-sectional view of the ratchet mechanism of FIG. 2.

FIG. 6 is a perspective view of the dental flossing apparatus of FIG. 1 with the ratchet mechanism of FIG. 2 in place.

DESCRIPTION OF THE PREFERRED EMBODIMENT

Figure 7:
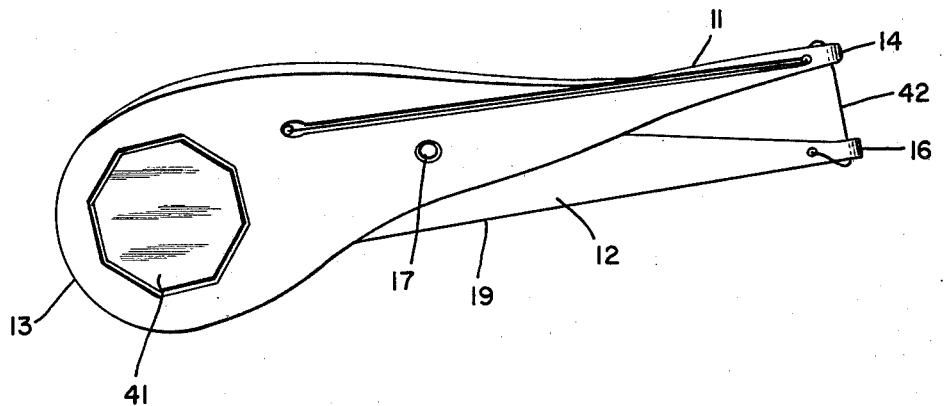
FIG. 7 is a bottom plan view of the dental flossing apparatus of FIG. 6.

In order to best understand the present invention it is necessary to refer to a description of its preferred embodiment in conjunction with the accompanying drawing. Referring to FIG. 1 the preferred embodiment of the present invention includes a first elongated member 11 and a second elongated member 12. The first elongated member 11 has a first end 13 which is adapted to receive a hexagonally shaped dental floss container in a hexagonally shaped hole and hold it snugly therein and a second end 14 which has a raised tip-portion having a hole which is disposed perpendicularly to the first elongated member 11 and adapted to receive dental floss therethrough. The second elongated member 12 has a first end 15 and a second end 16 which also has a raised tip-portion having a hole which disposed perpendiularly to the second elongated member and adapted to receive dental floss therethrough is formed so that when it is pivotally coupled by a rivet 17 to the first elongated member 11 in a scissor-like manner the raised tip-portion of the second elongated member 12 will separate from the raised tip-portion of the first elongated member 11 when the first ends 13 and 15 of the first and second elongated members 11 and 12 are brought together. At the first end 15 of the second elongated member 12 there is an inwardly facing pin 18.

Still referring to FIG. 1 the second elongated member 12 has an outer sidewall 19 which serves to keep the dental floss from becoming exposed and a groove 20 which travels longitudinally along the length of the second elongated member 12 and in which the dental floss is placed.

Referring now to FIG. 2 the preferred embodiment of the present invention also includes a dispensing device for controlling the dispensing of the dental floss from a dental floss container. The dispensing device includes a first portion of a shaft 21, which is adapted to be forceably engaged into a dental floss spool, a disc 22, which is adapted to travel circularly along an inner lip of the dental floss container and which is fixedly coupled to the first portion of the shaft 21, a second portion of the shaft 23, and a spool 24, which is mechanically coupled to the second portion of the shaft 23 and secured thereto by a rivet 25.

Referring now to FIG. 3 in conjunction with FIG. 1 one can note that the first elongated member 11 also has an outer sidewall 31, which serves to keep the dental floss from becoming exposed and a groove 32 which travels longitudinally along the length of the first elongated member 11 and in which the dental floss is placed. One can also note the raised tip-portions of both the first and second elongated members more clearly than by noting FIG. 1 alone.

Referring now to FIG. 4 the dispensing device is adapted to operate in conjunction with a dental floss container 41 which includes a spool of dental floss 42. The first portion of the shaft 21 is shown to be force-fitted into the spool of dental floss 42. The disc 22 is shown travelling on the inner lip of the dental floss container 41. The disc 22 has a series of spaced notches on its cylindrical sidewall which are exposed.

Referring to FIG. 5 in conjunction with FIG. 4 the spool 24 is shown mechanically coupled to the second portion of the shaft 23 by a ratchet assembly that includes a plurality of notches 51 on the inner cylindrical sidewall of the spool 24 and a pair of oppositely disposed extrusions on the outer cylindrical sidewall of the second portion of the shaft 23. The notches 51 and the two extrusions are aligned so that the spool will turn in only one direction.

Referring to FIG. 6 the preferred embodiment of the present invention is shown assembled. The hexagonally shaped dental floss container 41 is inserted into the hexagonally shaped hole adjacent to the first end 13 of the first elongated member 11 and is anchored snugly therein. The first portion of the shaft 21 is force-fitted into the spool of dental floss 42 and the disc 22 is placed onto the inner lip of the dental floss container 41. The dental floss 42 is pulled off the spool of dental floss and threaded into several holes in the second elongated member 12 travelling in the groove 20 thereof including the hole within the raised tip-portion thereof. The dental floss is then threaded across to the hole in the oppositely disposed raised tip-portion of the first elongated member 11 through several holes in the first elongated member 11 travelling in the groove 32 thereof to the spool 24, which serves as a take-up spool for the used dental floss. The inwardly facing pin near the first end 13 of the first elongate member 11 mechanically couples itself to one of the plurality of notches in the disc 22 when the first ends 13 and 15 of both the first and second elongated members 11 and 12 are brought together so that the disc 22 and the spool of dental floss 42 cannot turn. The spool 24 is mechanically coupled to a one-way ratchet assembly and may be turned in order to tighten the tension in the dental floss 42 between the dental floss container 41 and the spool 24. The length of dental floss 42 across the gap which is formed between the raised tip-portions of the first and second elongated members 11 and 12, may have tension applied thereto by a user, who merely squeezes the two first ends 13 and 15 together as much as he needs to achieve the tension that he requires for inserting the dental floss 42 between his teeth. He may then relax the tension in the length of dental floss 42 for added comfort while flossing. One of the advantages of this invention is that the user can vary the amount of tension in the length of dental floss 42 that he is using. Another advantage is that no length of dental floss 42 will go unused if this device is properly used.

Referring now to FIG. 7 in conjunction wih FIG. 6 the path of the dental floss 42 may be more clearly seen. As the dental floss 42 leaves the spool of dental floss 42 it travels in the groove 20 in the top surface of the second elongated member 12 to a hole therein and underneath to where it wraps once around the raised tip-portion thereof and enters the hole raised tip-portion. The dental floss 42 crosses the gap between the two raised tip-portions and enters the hole thereof. The dental floss then wraps once around the second raised tip-portion and enters a hole through which comes to the groove 32 in the bottom surface of the first elongated member 11 and travels therein to the spool 24.

Figure 8:
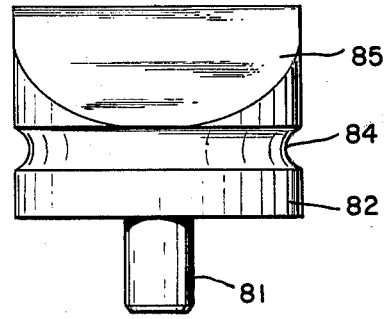
FIG. 8 is an elevational view of alternative tensioning mechanism for use with the dental flossing apparatus of FIG. 1 in place of the ratchet mechanism of FIG. 2.

Referring to FIG. 8 a second embodiment of the dispensing device is shown to include a shaft 81, which is adapted to be forced-fitted into a spool of dental floss 42, a disc 82, which is adapted to be force-fitted against the inner lip of the dental floss container 41, a spool 84, which is adapted to receive used dental floss 42, and thumb wheel 85 for turning the spool 84.

From the foregoing a tensioning mechanism for a dental flossing apparatus has been described. It should be noted that the figures and schematic are not drawn to scale, and distances of and between the figures are not to be considered significant.

Accordingly, it is intended that the foregoing disclosure and showing made in the drawing shall be considered only as illustrations of the principles of the invention. The invention is set forth with particularity in the appended claims.

What is claimed is:

1. In a dental flossing apparatus an improved tensioning mechanism for use in combination with dental floss on spool in a hexagonally shaped dental floss container having an inner lip, said improved tensioning mechanism comprising:
   a. a first elongated member, which has a hexagonally shaped hole at a first end in which the dental floss container is snugly placed and which has a raised tip-portion at a second end, said raised tip-portion having a hole which is disposed perpendicularly to said first elongated member and through which the dental floss passes;
   b. a second elongated member, which also has a first end and a second end, having a raised tip-portion at its second end that has a hole which is disposed perpendicularly to said elongated member and through which the dental floss passes, said second elongated member is formed so that when it is pivotally coupled to said first elongated member in a scissor-like manner said raised tip-portion of said second elongated member will separate from said raised tip-portion of said first elongated member when said first ends of said first and second elongated members are brought together;
   c. dispensing means for controlling the dispensing of the dental floss from the dental floss container, mechanically coupled to said first and second elongated members, said dispensing means comprising:
      a. a shaft which forceably engages the dental floss spool;
      b. a disc is positively placed into the floss container so that its peripheral edge is adjacent to the inner lip of the dental floss container, said disc is mechanically coupled to said shaft; and
      c. a collecting spool, which receives used dental floss, mechanically coupled to said shaft; and
      d. a ratchet system mechanically coupled to said collecting spool so that it allows said collecting spool to rotate in only one direction.

2. In a dental flossing apparatus an improved tensioning mechanism according to claim 1 wherein said collecting spool, said shaft and said disc formed one integral member and wherein also said disc forced fitted against the inner lip of the dental floss container.

* * * * *